US010960371B2

(12) United States Patent
Daliparthi et al.

(10) Patent No.: US 10,960,371 B2
(45) Date of Patent: *Mar. 30, 2021

(54) METHOD FOR PRODUCING DIHYDROXY COMPOUNDS

(71) Applicant: SABIC GLOBAL TECHNOLOGIES B.V., Bergen op Zoom (NL)

(72) Inventors: Surya Prakasa Rao Daliparthi, Bangalore (IN); Paulus Johannes Maria Eijsbouts, Bergen op Zoom (NL)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/589,977

(22) Filed: Oct. 1, 2019

(65) Prior Publication Data
US 2020/0164328 A1 May 28, 2020

Related U.S. Application Data

(63) Continuation of application No. 16/330,228, filed as application No. PCT/IB2017/055256 on Aug. 31, 2017, now Pat. No. 10,537,865.

(30) Foreign Application Priority Data

Sep. 5, 2016 (EP) ..................................... 16187242

(51) Int. Cl.
*B01J 8/00* (2006.01)
*B01J 8/02* (2006.01)
(Continued)

(52) U.S. Cl.
CPC ............. *B01J 8/0025* (2013.01); *B01J 4/004* (2013.01); *B01J 8/025* (2013.01); *B01J 8/0278* (2013.01);
(Continued)

(58) Field of Classification Search
CPC ... G02B 17/086; G02B 27/0093; G02B 27/141; G02B 2027/0178; G02B 27/0172;
(Continued)

(56) References Cited

U.S. PATENT DOCUMENTS 4,618,418 A * 10/1986 Heijnen ................ C02F 3/2806
210/151
5,395,857 A 3/1995 Berg et al.
(Continued)

FOREIGN PATENT DOCUMENTS

CN 101213988 A 7/2008
CN 101885532 A 11/2010
(Continued)

OTHER PUBLICATIONS

International Search Report for International Application No. PCT/IB2017/055256, International Filing Date Aug. 31, 2017, dated Oct. 19, 2017, 5 pages.
(Continued)

*Primary Examiner* — Huy Tram Nguyen
(74) *Attorney, Agent, or Firm* — Cantor Colburn LLP

(57) ABSTRACT

The disclosure is directed to the use of an upflow reactor for producing a dihydroxy compound, to a method for producing a dihydroxy compound, and to a method for manufacturing polycarbonate. The upflow reactor for producing a dihydroxy compound of the disclosure comprises: a vessel; a catalyst bed disposed in said vessel; a distributor in fluid communication with an inlet through which reactants are introduced to said distributor, said distributor being disposed at a lower end of said vessel and comprising distributor perforation(s) disposed in said distributor, at least part of which distributor perforations are in a direction facing away from said catalyst bed; and a collector through which said
(Continued)

product dihydroxy compound is removed, said collector being disposed at an upper end of said vessel.

20 Claims, 12 Drawing Sheets

(51) Int. Cl.
*B01J 4/00* (2006.01)
*C07C 37/60* (2006.01)
*C07C 39/16* (2006.01)

(52) U.S. Cl.
CPC ............ *B01J 8/0292* (2013.01); *C07C 37/60* (2013.01); *C07C 39/16* (2013.01); *B01J 2208/00911* (2013.01); *B01J 2208/06* (2013.01)

(58) Field of Classification Search
CPC .. G02B 2027/0187; H04N 5/33; G06F 3/013; B01J 8/0025; B01J 8/0292; B01J 8/0278; B01J 4/004; B01J 2208/06; B01J 2208/00911; B01J 8/025; C07C 39/16; C07C 37/60

USPC ........................................................ 422/220
See application file for complete search history.

(56) References Cited

U.S. PATENT DOCUMENTS

| | | | |
|---|---|---|---|
| 7,371,894 B2 | 5/2008 | Wonders et al. | |
| 2004/0068085 A1* | 4/2004 | Belfadhel | ............. B01J 8/0292 528/196 |

FOREIGN PATENT DOCUMENTS

| | | |
|---|---|---|
| CN | 202638404 U | 1/2013 |
| CN | 203971921 U | 12/2014 |
| WO | 2004033084 A1 | 4/2004 |
| WO | 2016046834 A1 | 3/2016 |

OTHER PUBLICATIONS

Written Opinion for International Application No. PCT/IB2017/055256, International Filing Date Aug. 31, 2017, dated Oct. 19, 2017, 5 pages.

* cited by examiner

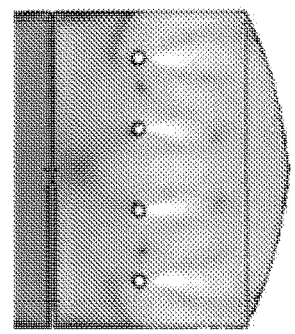
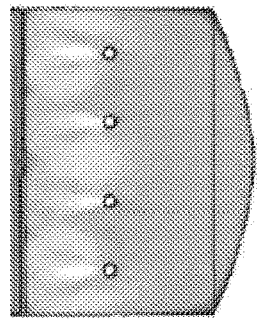
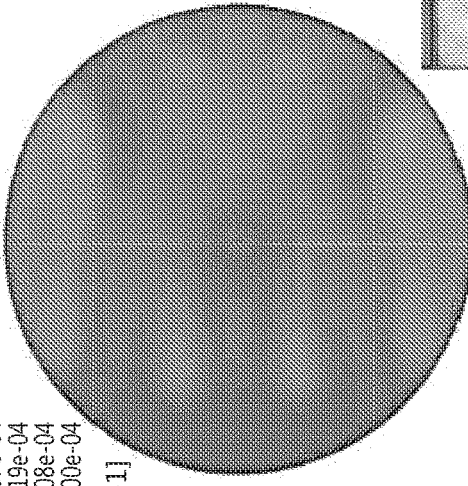
Fig. 12
Just above the distributor
Aperture bias & Reserve flow
Mal distribution = 134%
Just above the distributor
Aperture bias & Normal feed flow
Mal distribution = 223%
Velocity abovedistcontour
9.000e-01
5.268e-01
3.083e-01
1.805e-01
1.056e-01
6.183e-02
3.619e-02
2.118e-02
1.240e-02
7.258e-03
4.248e-03
2.487e-03
1.456e-03
8.519e-04
4.987e-04
2.919e-04
1.708e-04
1.000e-04
[m s^-1]

Fig. 15
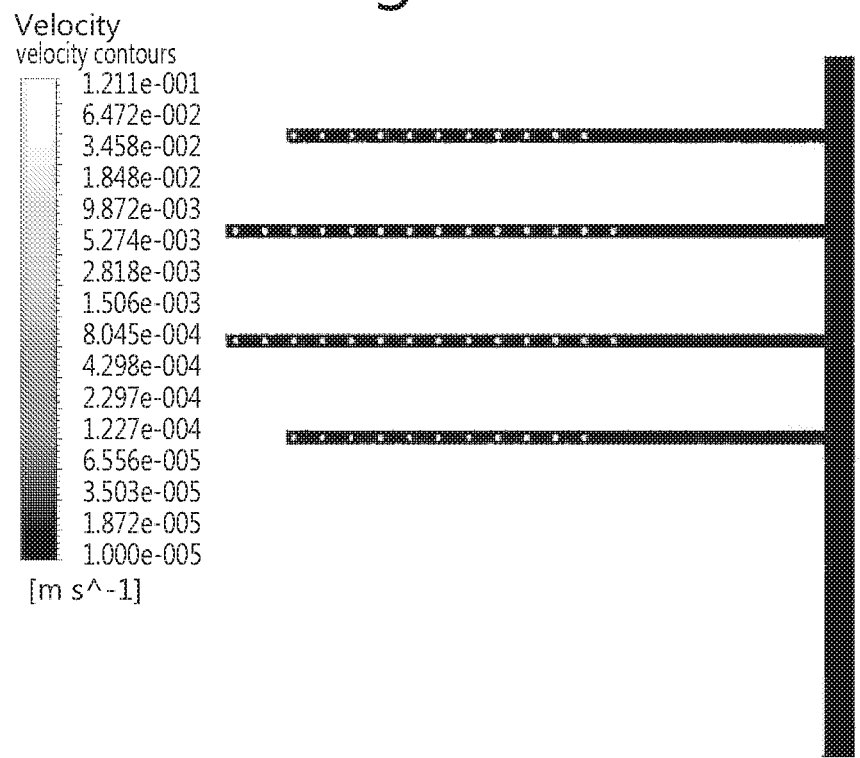
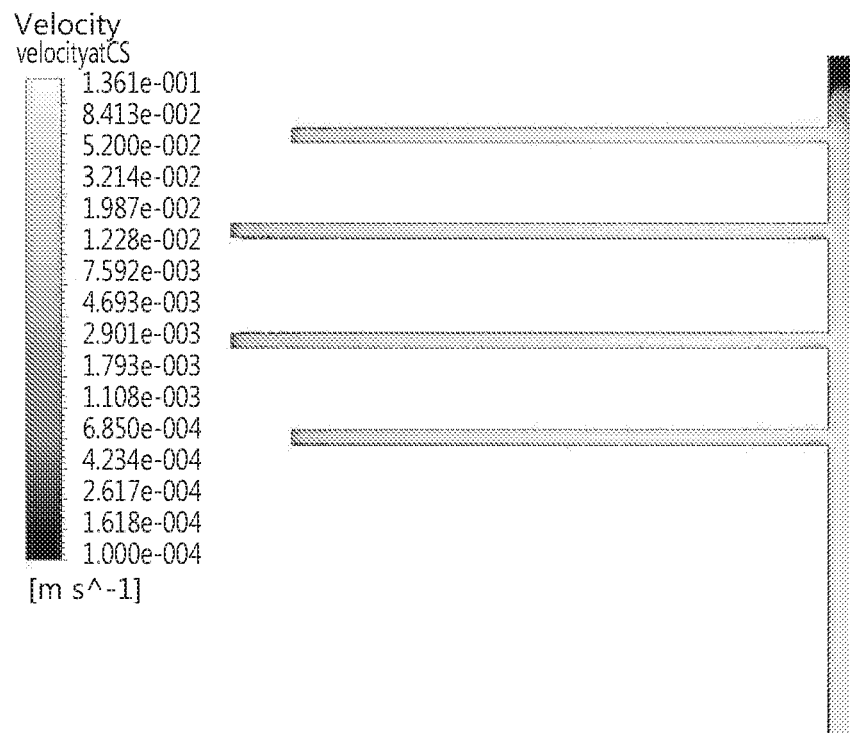

METHOD FOR PRODUCING DIHYDROXY COMPOUNDS

This application is continuation application of U.S. application Ser. No. 16/330,228 filed on Mar. 4, 2019, which is a 371 of International Application No. PCT/IB2017/055256, filed Aug. 31, 2017, and which claims priority to European Application Ser. No. 16187242.9 filed Sep. 5, 2016, all of which are incorporated by reference in their entirety.

The disclosure is directed to the use of an upflow reactor for producing a dihydroxy compound, to a method for producing a dihydroxy compound, and to a method for manufacturing polycarbonate. More in particular, the disclosure relates to the production of bisphenol A by introduction of a ketone and a phenol compound in an upflow reactor.

Dihydroxy compounds, an in particular bisphenols, are used as raw materials in the preparation of chemical products such as epoxy resins and polycarbonates. They are commonly prepared by the condensation of ketones and phenols. Typical bisphenols include 2,2-bis(4-hydroxyphenyl) propane (also known as bisphenol A), which can be produced by reacting acetone (also known as dimethyl ketone) and a phenol in the presence of an acid.

A packed bed reactor system utilised in the production of bisphenols generally comprises a bed of packed materials such as, for example, catalyst that may be particulate in form (e.g., beaded), to which liquid reactants are introduced. The reactants are made to flow through the bed where they contact each other in the presence of the catalyst and react to form a final product that is removed from a downstream point in the bed. In such packed bed reactor systems, pressure associated with the bed often has an effect on the physical performance of the reactor. Differential pressure, which is a measure of the resistance to flow over the height of the packed bed, increases with increased bed height. The differential pressure over the height of the packed bed may compress and deform the catalyst beads causing a reduction in liquid throughput as a result of pressure drop increase due to the loss of free void volume in the bed.

Reactors for the manufacture of bisphenol A usually operate in a downflow mode, where the exothermic condensation of phenol and acetone occurs in the presence of an acidic ion exchange resin catalyst and optionally in the presence of a co-catalyst promoter. When producing bisphenol A in a downflow mode, the degree of crosslinking of certain ion exchange resin catalysts directly affects the physical performance of the reactor as well as the reactivity, the selectivity, and the yield of this reactor. Indeed, increasing the throughput of the bisphenol A reactors operated in downflow configurations involves an increase in pressure drop and an increased risk that the beads will be misshapen and/or that the packed bed will be compressed and loose free void volume. Hydraulic limitations have also been observed, particularly in the case of the ion exchange resin catalyst having a low degree of crosslinking (e.g., less than or equal to about 2.5%). Although the hydraulic problems are less significant in ion exchange resin catalysts having higher degrees of crosslinking, the reactivity, selectivity and lifetime (ton produced per ton of catalyst used) of such resins in the synthesis of bisphenol A also decreases considerably. As such, a more highly crosslinked catalyst is generally more resistant to the hydraulic impact attributable to the particle shape and to the compression mechanism of the particle beads due to pressure.

However, higher crosslinked catalyst also tends to be characterised by lower reactivity, lower selectivity, and shortened lifetime.

In an effort to compensate for the hydraulic limitations of catalysts having a lower degree of crosslinking while at the same time retaining the benefits of catalysts having a higher degree of crosslinking, bisphenol A may be produced in a "combi-bed" apparatus, as is disclosed in U.S. Pat. No. 5,395,857. The combi-bed apparatus optimises the high production rate of bisphenol A indicative of a catalyst having a high degree of crosslinking as well as the increased activity, selectivity, and lifetime of a catalyst having a lower degree (less than or equal to about 2%) of crosslinking by combining both catalysts in the same reactor bed. Nevertheless, the capabilities of the combi-bed apparatus remain limited in terms of lifetime and in terms of maximum allowable throughput.

In further attempts to alleviate the problems associated with hydraulic limitations in catalyst beds, reactors have also been constructed to have an increased diameter while maintaining a decreased bed height, thereby allowing the reactors to utilise catalyst having a lower degree of crosslinking while operating with a pressure drop that enables acceptable reactor throughput to be maintained. In still further attempts to alleviate the problems associated with hydraulic limitations, reactants may be fed to bisphenol A reactors in an upflow mode to reduce the effects of pressure drop on the performance of the reactors and to overcome throughput limitations.

An upflow reactor for the production of dihydroxy compounds is, for instance, disclosed in WO-A-2004/033084, the content of which is herewith completely incorporated by reference. This document describes a reactor that includes a vessel, a catalyst bed disposed within the vessel, and a reactant distribution/product collection system disposed within the vessel. The reactant distribution/product collection system includes a distributor disposed at a lower end of the reactor and a collector disposed at an upper end of the reactor. Both the distributor and the collector each include a perforation. Screens are disposed over the perforations. In use, the distributor directs the reactant from the distributor upward through a catalyst bed.

U.S. Pat. No. 4,618,418 discloses a single unit fluidized-bed reactor having a reaction space for purification of waste water with biomass attached to carrier particles, comprising a liquid distribution device above the bottom of the reaction space particularly suited for introduction of waste water in wide reactors to achieve uniform fluidization therein, said device consisting of a number of substantially horizontal pipes, each having in the under-surface a number of regularly distributed openings for downward introduction of the liquid, and on top of the reaction space united therewith a multi-functional separation compartment for complete separation of the gas-liquid-solids mixture leaving the reaction space and for complete return of attached biomass into the reaction space, the separation compartment being construction so as to handle treatments involving large or small gas fractions in reactors of varying width.

The inventors found that the existing reactors for producing dihydroxy compounds suffer from limited throughput amongst others due to pressure drop limitations. Furthermore, the inventors found that the flow distribution throughout the existing reactors is insufficiently uniform.

An objective of the disclosure, therefore, is to improve the throughput of a reactor for producing dihydroxy compounds.

Further objective of the disclosure is to improve the uniform flow distribution throughout a reactor for producing dihydroxy compounds.

The inventors surprisingly found that one or more of these objectives can, at least in part, be met by an upflow reactor wherein the reactants are introduced into the reactor in a specific direction.

Accordingly, in a first aspect the disclosure is directed to the use of an upflow reactor for producing a dihydroxy compound, said upflow reactor comprising:
- a vessel;
- a catalyst bed disposed in said vessel; and
- a distributor in fluid communication with an inlet through which reactants are introduced to said distributor, said distributor being disposed at a lower end of said vessel and comprising one or more distributor perforations disposed in said distributor, at least part of which distributor perforations are in a direction facing away from said catalyst bed; and
- a collector through which said product dihydroxy compound is removed, said collector being disposed at an upper end of said vessel.

The inventors believe that when distributor perforations are facing upwards on the distributor, i.e. facing the catalyst bed, the jets of liquid that are coming out of those distributor perforations influence the flow distribution above the distributor. Without wishing to be bound by any theory, the inventors believe that the momentum of those liquid jets is responsible for higher mal-distribution (defined as the uneven dispersion of flow through a cross-sectional slice of the reactor) above the distributor and dissipating this momentum would help to reduce the mal-distribution. In order to dissipate the momentum, distributor perforations were provided in a direction facing away from the catalyst bed (e.g. in a direction pointing downwards towards the vessel bottom). When the liquid jets impinge on the vessel wall (such as the bottom wall), momentum gets dissipated.

The reactor in accordance with the disclosure includes a bed of catalyst through which the reactants flow to react and produce the final dihydroxy compounds. The reactants flow in the generally vertical direction co-currently through the bed from a lower elevation to a higher elevation. To obtain favourable selectivity, yield, and reactant conversion, the reactor is designed such that a flow profile resembling or at least approximating plug flow can be achieved. The upflow reactor as described herein is highly suitable for producing a bisphenol compound. Although the method is applicable to the production of any isomer of bisphenol, the preferred isomer is bisphenol A produced by the reaction of a ketone (e.g., acetone) with a phenol in the presence of a catalyst and optionally in the presence of a co-catalyst (e.g., a reaction promoting agent). Typical phenols that may be utilised include, but are not limited to, ortho-cresol, meta-cresol, 2,6-dimethylphenol, ortho-sec-butylphenol, 1,3,5-xylenol, tetramethylphenol, 2-methyl-6-tert-butylphenol, ortho-phenylphenol, ortho- and meta-chlorophenol, ortho-bromophenol, 2,6-dichlorophenol, and any combination thereof. The reactants in the context of the present disclosure are preferably acetone and phenol the reaction of these resulting in bisphenol A as a main and desired reaction product. The finished bisphenol A product may be further combined with phosgene or diphenyl carbonate to produce a polycarbonate.

FIG. 1 shows one exemplary embodiment of an upflow chemical reactor 10 utilised to produce the preferred bisphenol isomer. Reactor 10 includes a catalyst bed 12, a distributor 20, and a collector 40. Screens can provide for the containment of the catalyst within the reacting area such that the reaction mixture can flow through the reactor. A free liquid space 13 may be defined above catalyst bed 12 in the upper part of reactor 10. The reactants (preferably acetone and phenol) are jetted into the reactor via distributor 20 in a downward direction, away from the catalyst bed. The bottom wall of the reactor in this embodiment serves as an impingement plate dissipating momentum. Reactants travels downward from the distributor and impinges on the reactor bottom wall where momentum is dissipated, before the reactants travel upwards and through the catalyst bed 12 to free liquid space 13. This configuration is such that the mal-distribution of flow is minimised and a substantially uniform flow profile is maintained over any interstitial slice of catalyst bed 12. In order to minimise the amount of catalyst required for the most cost effective operation of reactor 10, catalyst bed 12 extends over a height h such that the product bisphenol isomer at the uppermost level of catalyst bed 12 is of the desired yield and selectivity.

Catalyst bed 12 is contained by a vessel 14. Vessel 14 may be of any geometry capable of facilitating the flow of reactants in a net upflow configuration. For example, vessel 14 may be substantially cylindrical, parallelepiped, or spherical in structure. Because cylindrically shaped vessels are widely available in the chemical industry, and because existing tanks or reactors can be converted into upflow reactors according to the disclosure with relatively simple modifications, it is preferred that vessel 14 is of a cylindrical geometry. The lower end of vessel 14 is preferably flat (as shown in FIG. 1). The lower end may, however, be rounded, conical, or any combination thereof. Distributor 20 is disposed at a lower end of vessel 14. The term "lower end" as used in this context is meant to refer to the lower half of the vessel. This means that the vessel volume above distributor 20 is larger than the vessel volume below distributor 20. Collector 40 is disposed at an upper end of vessel 14. The term "upper end" as used in this context is meant to refer to the upper half of the vessel. This means that the vessel volume above collector 40 is smaller than the vessel volume below collector 40.

The catalyst disposed in vessel 14 is preferably at least a partially crosslinked ion exchange resin catalyst. The degree of crosslinking of the ion exchange resin catalyst is typically maintained at a level so as to preserve the integrity of the spherically shaped particles. In particular, the degree of crosslinking may be up to about 4%. Lower levels of crosslinking, however, improve catalyst life, and therefore the degree of crosslinking is preferably about 2%. It is more preferred that the catalyst is a sulphonated aromatic resin, such as polystyrene, containing some degree of divinylbenzene crosslinking and some degree of sulphonic acid functionality. The crosslinking density is most preferably 2.5% or less, and the acid milliequivalency is preferably 4 milliequivalents per gram (meq/g) or more. Optionally, co-catalysts may also be used. Typical co-catalysts (which may or may not be attached) include, but are not limited to, thiols and mercaptans. The reactor in the present disclosure is operated as a fixed bed, also known as packed bed, reactor and thus should be distinguished from a fluidised bed wherein the catalyst is brought in a fluidised state. To the contrary the catalyst particles in the reactor used in the disclosure are not brought in such a fluidised state. A skilled person will, however, appreciate that in a fixed bed or packed bed operation mode there may be some unintentional catalyst displacement caused by the flow of reactants through the catalyst bed. Such displacement is not considered as a state of fluidisation.

The reactor of the disclosure may comprise a distributor screen 17 disposed between said distributor 20 and said catalyst bed 12. Distributor screen 17 preferably comprises mesh material or a flat plate that substantially corresponds to the cross sectional geometry of vessel 14. Preferably, distributor screen 17 is placed directly above distributor 20. The distributor screen 17 can thus be in direct contact with distributor 20, but it is preferred that there is some distance between distributor screen 17 and distributor 20, such as a distance of 5-300 mm, or 10-200 mm.

Upon introduction of the reactants through the one or more distributor perforations of distributor 20, the liquid jets of reactants impinge on the vessel wall (such as the bottom wall) and momentum gets dissipated. Subsequently, the reactants flow through distributor screen 17, resulting in a highly uniform flow distribution before passing catalyst bed 12. The size of the openings in screen 17 can suitably be ⅔ to ⅙ of the minimum particle diameter of the catalyst beads in the reaction mixture, such as ½ to ¼ of the minimum particle diameter of the catalyst beads in the reaction mixture, with less than ⅓ of the minimum diameter being preferred in order to discourage the receiving of the catalyst particles in distributor 20. For a catalyst having a particle size of 400-800 µm in diameter, the openings in screen 17 are preferably 100-200 µm, with 150 µm or less being preferred. The distributor screen can have openings of 50-300 µm, and may have a porosity of 10-50% open area. Different types of distributor screens may be employed in accordance with the disclosure, including mesh type distributor screens, slot type distributor screens, array type distributor screens, tubular type distributor screens, and combinations thereof. The distributor screen may have different shapes, such as a flat shape, a cone shape, or a tubular shape.

The use of at least one further distributor screen provided between the first distributor screen and the collector may aid in reducing dead spaces in the reactor top section, and thereby provide better flow distribution.

A packing material (not shown) may optionally be disposed within vessel 14 and interspersed within the catalyst. The packing material, which is generally rigid, bears the weight of the catalyst with which the packing material is interspersed, thereby affording the catalyst additional structural support within catalyst bed 12 by inhibiting the compression of the catalyst under its own weight. Because of the difficulties encountered by the separation of the catalyst from the packing materials, packing materials are generally used only with catalysts having low crosslinking. A typical packing material comprises a plurality of discrete objects dumped within the vessel of a reactor resulting in a random arrangement of surfaces and providing tortuous paths for the flow of the reactant materials. The objects may be fabricated from any rigid chemically inert, and thermally stable material that allows for optimum contact of the reactant materials with each other and with the catalyst as they flow through the catalyst bed. Optimum contact is generally realised by objects having large void fractions (objects that are small in volume and have large surface areas). Preferred packing materials include, but are not limited to, Pall rings, Tellerette rings, Raschig rings, Berl saddles, Intalox saddles, and combinations thereof.

An inlet 18 is disposed at a lower end of catalyst bed 12 to facilitate the introduction of the reactants to reactor 10. Inlet 18 may be a node at which tubing, piping, jets, or similar devices form a juncture that allows for the flow of reactants into the reaction zone defined by catalyst bed 12. Preferably, inlet 18 receives the reacting mixture and directs it into the reactor 10 through distributor 20. When passing catalyst bed 12, the desired dihydroxy compound is produced. An outlet 22 is disposed at an upper end of catalyst bed 12, directly in catalyst bed 12, in free liquid space 13, or in a combination thereof, preferably above the screen 47. Outlet 22 provides for the removal of the product isomer from reactor 10 by receiving the isomer through a collector 40.

Distributor 20 comprises distributor perforations in a direction facing away from the catalyst bed. Hence, the distributor perforations may for instance be in a direction pointing downwards, towards the bottom of vessel 14. However, the distributor perforations can point in any direction that faces away from the catalyst bed. A hemisphere under the plane defined by the catalyst bed can be defined, which represents the possible directions in which the distributor perforations are directed. While any of these directions defined by such hemisphere is possible, it is preferred that the distributor perforations point downward, towards the bottom of vessel 14.

The amount of distributor perforations in the distributor may vary, but is preferably 50 perforations per $m^2$ or more, such as 80 perforations per $m^2$ or more, preferably 100-200 perforations per $m^2$.

The dimensions of the distributor perforation are preferably such that the mass flow through each perforation is substantially the same. In order to achieve good flow distribution across the cross section of the reaction vessel, it is needed to introduce the feed uniformly across the cross section. Different lengths of flow paths in the distributor can lead to significant variation in the flow through these distributor perforations. This is because the resistance to the flow is different in the different pathways. Therefore, it is preferred that the mass flow through each perforation is substantially the same. This may, for instance, be accomplished by playing with the perforation diameters to maintain uniform flow resistances.

Optionally, the reactor can further comprise at least a second distributor between said first distributor and said collector, wherein said second distributor is in fluid communication with a second inlet through which reactants are introduced to said second distributor. Like the first distributor, the second distributor may comprising one or more perforations disposed in said second distributor. In an embodiment, the catalyst bed comprises two or more sections of catalyst bed, wherein beneath each section a distributor may be provided. In such case, the one or more additional distributors may, for instance, have perforations that are directed sideways so that liquid jets coming out of the distributor perforations impinge on the side wall of the vessel where momentum gets dissipated. In this way one can avoid considerable disturbance of catalyst bed sections below each additional distributor.

The reactor may further comprising one or more further distributor screens 37 between said the first distributor screen and the collector. Preferably, the further distributor screen comprises openings with a diameter of 50-300 µm and has a porosity of 10-50% open area. Like the distributor screen, the different types of further distributor screens may be employed, including mesh type distributor screens, slot type distributor screens, array type distributor screens, tubular type distributor screens, and combinations thereof. The further distributor screens may have different shapes, such as a flat shape, a cone shape, or a tubular shape.

FIGS. 2A and 2B show examples of configurations that provide a uniform flow distribution of the reaction mixture across the section of the reactor. Distributor 20 comprises a manifold 28 into which reactant material is received through a manifold inlet 30 disposed in fluid communication with the inlet of the reactor. In one exemplary embodiment of distributor 20, distribution arms 32 extend laterally from manifold 28. Distribution arms 32 disposed proximate opposing ends of manifold 28 are generally dimensioned to be shorter than the arms disposed proximate the centre of manifold 28. As such, the outer defining edges of distributor 20 preferably corresponds to the cross sectional geometry of a cylindrical reactor. In particular, if the cross sectional dimension of the reactor is round, distribution arms 32 are generally dimensioned such that the outer ends of each extend from the inner surface of the reactor approximately the same distance to cause distributor 20 to approximate a circular shape when installed into the reactor and viewed from the upper- or lower end of the reactor.

Manifold 28, as well as distribution arms 32, are preferably fabricated of piping having distribution perforations 34 that enable fluid communication to be maintained between inlet manifold 30 and the catalyst disposed in the reactor bed.

Aggregate layers may optionally be disposed at a lower end of catalyst bed 12. Aggregate layers provide support to catalyst bed 12 and comprise a material that is essentially inert to the reactants and products produced in reactor 10. The material that comprises aggregate layer 16 may be, but is not limited to, silica sand, diatomaceous earth, ceramic balls, and combinations thereof.

FIG. 3 shows an example of a collector 40. Collector 40 may be a simple effluent pipeline, but is preferably similar in structure to the distributor shown in FIG. 2 in order to reduce problems associated with dead volumes that could appear when flow out of the reactor is reduced from the catalyst bed to the effluent pipeline. It also allows good distribution of fluids in case a downflow mode has to be applied to the vessel. Collector 40 is positions proximate the upper end of the reactor in fluid communication with an outlet of the reactor. Reaction products (dihydroxy compounds, e.g., bisphenol A and isomers) produced from the reaction of acetone and phenol (as well as non-reacted components) are removed from the reactor through collector 40.

Collector 40 preferably comprises a manifold 42 having collection arms 44 extending therefrom. Preferably, collection arms 44, as well as manifold 42, include collector perforations 46 such that the dihydroxy compound product can be received therein and removed through a product takeoff line 48. In an exemplary embodiment of collector 40, collection arms 44 extend laterally from manifold 42. Collection arms 44 disposed proximate opposing ends of manifold 42 are generally dimensioned to be shorter than the arms disposed proximate the centre of manifold 42. As such, the outer defining edges of collector 40 may correspond to the cross sectional geometry of a cylindrical reactor. As with the distributor, the ends of collections arms 44 may approximate the geometry of the inner surface of the reactor.

Preferably, collector 40 comprises one or more collector perforations disposed in said collector. These collector perforations may be disposed in said collector in a direction facing away from the said catalyst bed. Hence, the collector perforations may for instance be in a direction pointing upwards, towards the top of vessel 14. However, the distributor perforations can point in any direction that faces away from the catalyst bed. A hemisphere above the plane defined by the catalyst bed can be defined, which represents the possible directions in which the collector perforations are preferably directed. While any of these directions defined by such hemisphere is possible, it is preferred that the collector perforations point upward, towards the top of vessel 14.

One or more second screens 47 may be disposed at said collector (collector screens). It is possible to dispose said second screens 47 at any point intermediate distributor screen 17 and collector 40. Second screens 47 preferably comprise mesh material of flat plates that substantially correspond to the cross sectional geometry of vessel 14 and are preferably placed directly below collector 40, as is shown in FIG. 1. The size of the openings in screens 47 can suitably be $2/3$ to $1/6$ of the minimum particle diameter of the catalyst beads in the reaction mixture, such as $1/2$ to $1/4$ of the size of the minimum particle diameter of the catalyst beads in the reaction mixture, with less than $1/3$ of the minimum diameter being preferred in order to discourage the receiving of the catalyst particles in collector 40. For a catalyst having a particle size of 400-800 µm, the openings in one or more collector screens 47 can be 100-200 µm, with 150 µm or less being preferred. A collector screen 47 can have openings of 50-300 µm, and may have a porosity of 10-50% open area. Different types of collector screens 47 may be employed in accordance with the disclosure, including mesh type screens, slot type screens, array type screens, tubular type screens, and combinations thereof. The one or more collector screens 47 may have different shapes, such as a flat shape, a cone shape, or a tubular shape.

In operation, a reacting mixture comprises a ketone and a fresh and/or recycled phenol (e.g. acetone and phenol) is introduced into reactor 10 through inlet 18. The operation of the reactor may be "single-pass", e.g., the ketone and phenol may be fed to the reactor and the dihydroxy compound and excess reactants removed at the reactor outlet. Preferably, however, the operation of the reactor includes a recirculation loop, e.g., the dihydroxy compound is removed at the reactor outlet and the excess ketone and phenol are recycled back to the reactor feed. The pressure at which the reactants are introduced is sufficient to force the reactants out of distributor 20, through the catalyst bed 12, and to collector 40. The composition of the fed reactants can be monitored to ensure that proper specifications are met for the production of the desired dihydroxy compound. Monitoring of the reactants may be either inline or by the removal of samples from the inlet streams.

Temperature and pressure can be monitored at inlet 18, at various points within catalyst bed 12, at free liquid space 13 (if any), and at outlet 22. Flow rates may also be monitored. If the operation of reactor 10 is automated, the measurements can be utilised to control the feed rates of the reactants to inlet 18, as well as other parameters of the system.

It is preferred that the temperature at the top of catalyst bed 12 is higher than the dihydroxy compound crystallisation temperature. In order to obviate the problems associated with the crystallisation of product, or in case the reactor insulation is insufficient, reactor 10 may be heated, particularly at the top portion thereof, by passing a hot fluid stream through a reactor jacket. The hot fluid stream passed through the jacket can then transfer heat to the reaction mixture and prevent crystallisation of the dihydroxy compound in the catalyst bed. As alternative, electrical tracing can be used to maintain a sufficiently high wall temperature preventing crystallisation.

In a further aspect, the disclosure relates to a method for producing a dihydroxy compound in an upflow reactor according to the disclosure, said method comprising:
   introducing a reactant through said inlet to said distributor;

flowing said reactant through said catalyst bed; and
recovering said dihydroxy compound from said collector.

The method for producing a dihydroxy compound is preferably a method for producing a bisphenol compound such as in particular bisphenol A.

In yet a further aspect, the disclosure is directed to a method for manufacturing polycarbonate, said method comprising:

producing a dihydroxy compound according to a method for producing a dihydroxy compound as described above, and reacting said dihydroxy compound with a carbonate source such as phosgene or diphenyl carbonate.

The method for manufacturing polycarbonate, preferably comprises producing a bisphenol compound such as bisphenol A, and reacting the bisphenol compound with phosgene, a diphenyl carbonate, or a combination thereof.

All references cited herein are hereby completely incorporated by reference to the same extent as if each reference were individually and specifically indicated to be incorporated by reference and were set forth in its entirety herein.

The use of the terms "a" and "an" and "the" and similar referents in the context of describing the disclosure (especially in the context of the claims) are to be construed to cover both the singular and the plural, unless otherwise indicated herein or clearly contradicted by context. The terms "comprising", "having", "including" and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure. For the purpose of the description and of the appended claims, except where otherwise indicated, all numbers expressing amounts, quantities, percentages, and so forth, are to be understood as being modified in all instances by the term "about". Also, all ranges include any combination of the maximum and minimum points disclosed and include and intermediate ranges therein, which may or may not be specifically enumerated herein.

Preferred embodiments of this disclosure are described herein. Variation of those preferred embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject-matter recited in the claims appended hereto as permitted by applicable law. Moreover, any combination of the above-described elements in all possible variations thereof is encompassed by the disclosure unless otherwise indicated herein or otherwise clearly contradicted by context. The claims are to be construed to include alternative embodiments to the extent permitted by the prior art.

For the purpose of clarity and a concise description features are described herein as part of the same or separate embodiments, however, it will be appreciated that the scope of the disclosure may include embodiments having combinations of all or some of the features described.

The disclosure will now be further illustrated by the following non-limiting examples.

DESCRIPTION OF THE FIGURES

FIG. 2: Schematic view of reactant distributors, where

FIG. 12: Snapshot comparison of velocity contours on a cross sectional plane located 10 mm above the distributor screen; with perforations facing upwards (left) and with apertures facing downward (right).

FIG. 15: Velocity contours on surface (left) and the velocity contours on a sectional plane (right) of pipe network model.

EXAMPLES

Reactor Geometry

Figure 1:
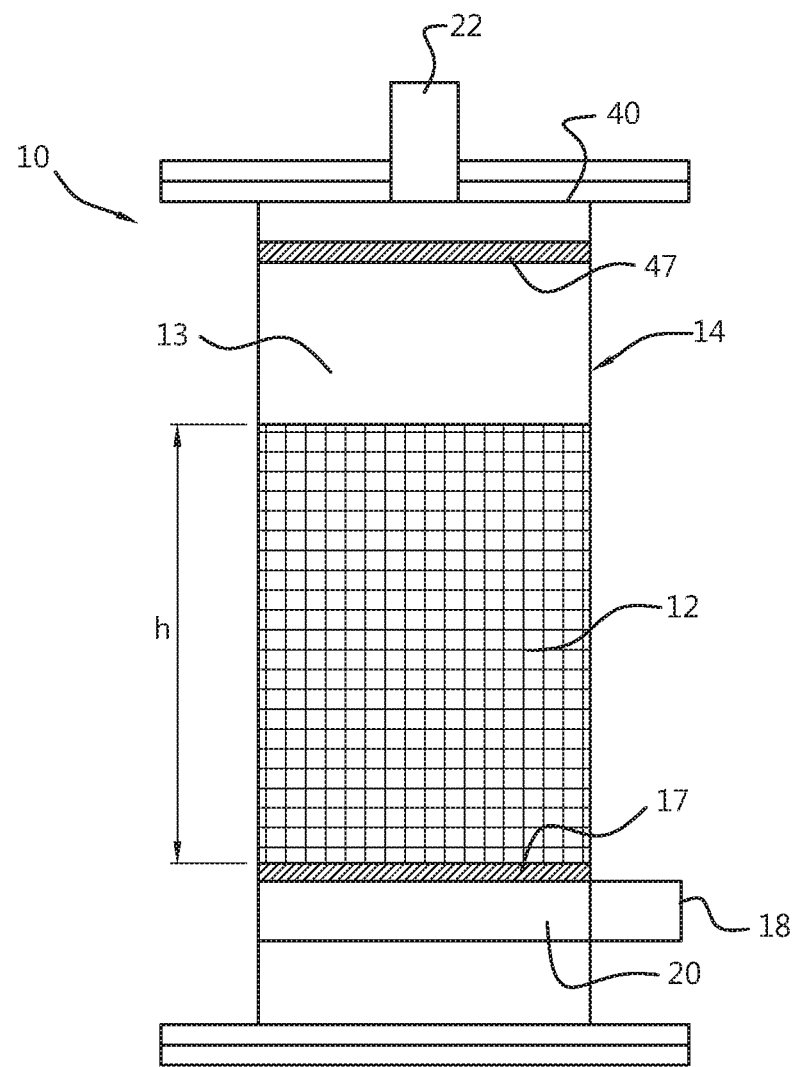
FIG. 1: Schematic view of one exemplary embodiment of an upflow chemical reactor.
Figure 2A:
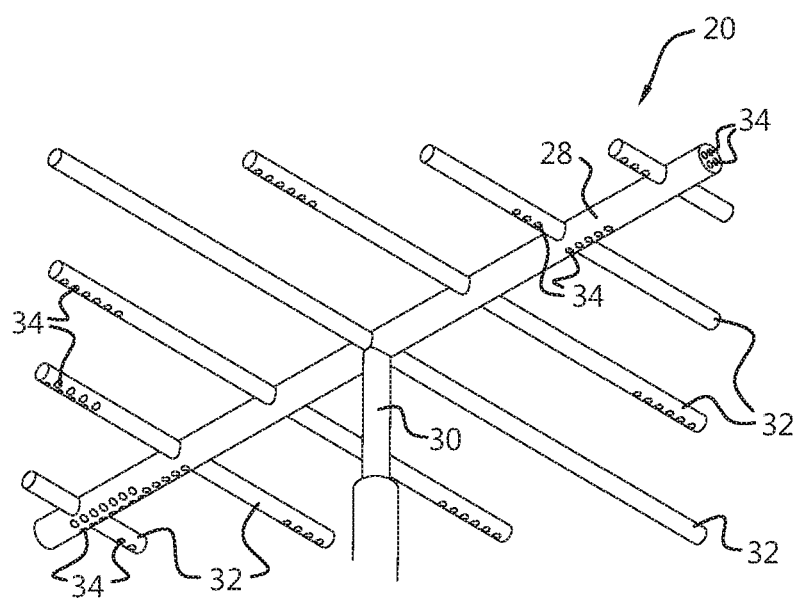
FIG. 2A is a snapshot of distributor 20 and FIG. 2B is a snapshot of a distributor 20 in a reactor.
Figure 2B:
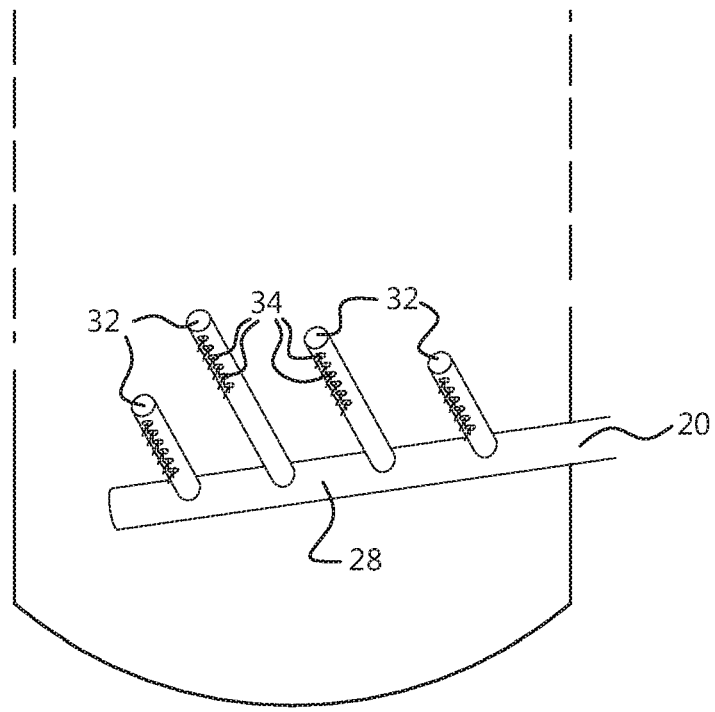
Figure 3:
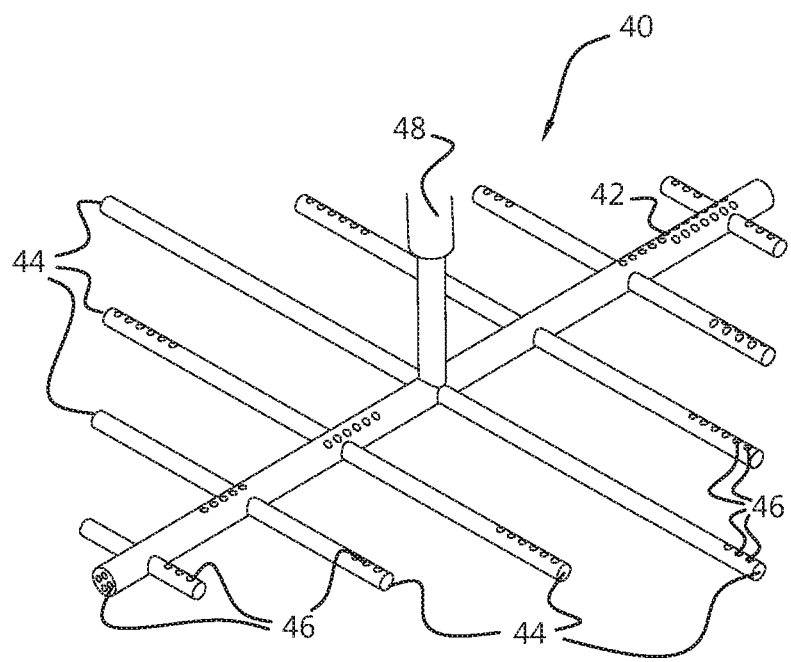
FIG. 3: Schematic view of a product collector.
Figure 4:
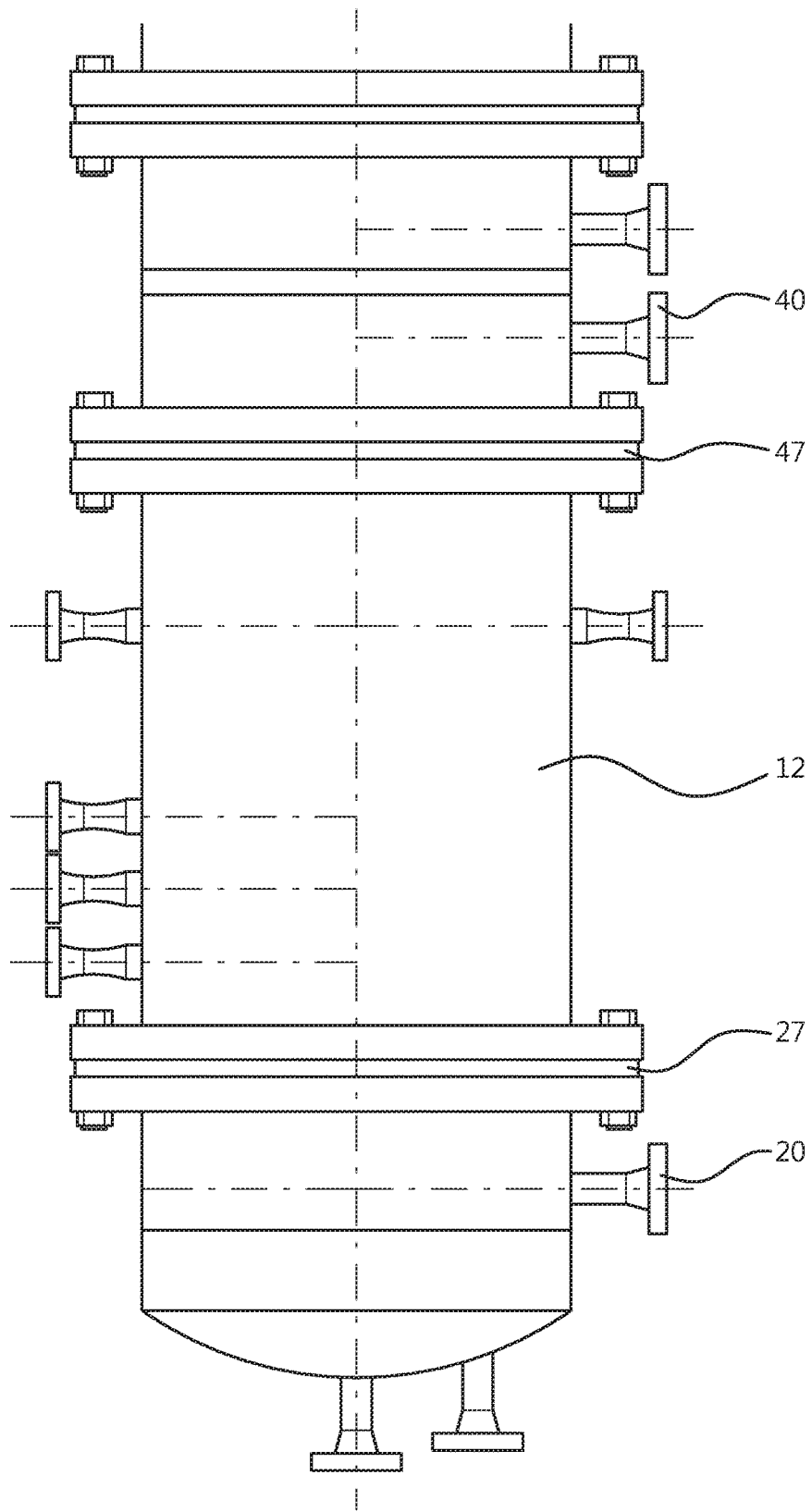
FIG. 4: Snapshot of a single stage drawing in upflow reactor.
Figure 5:
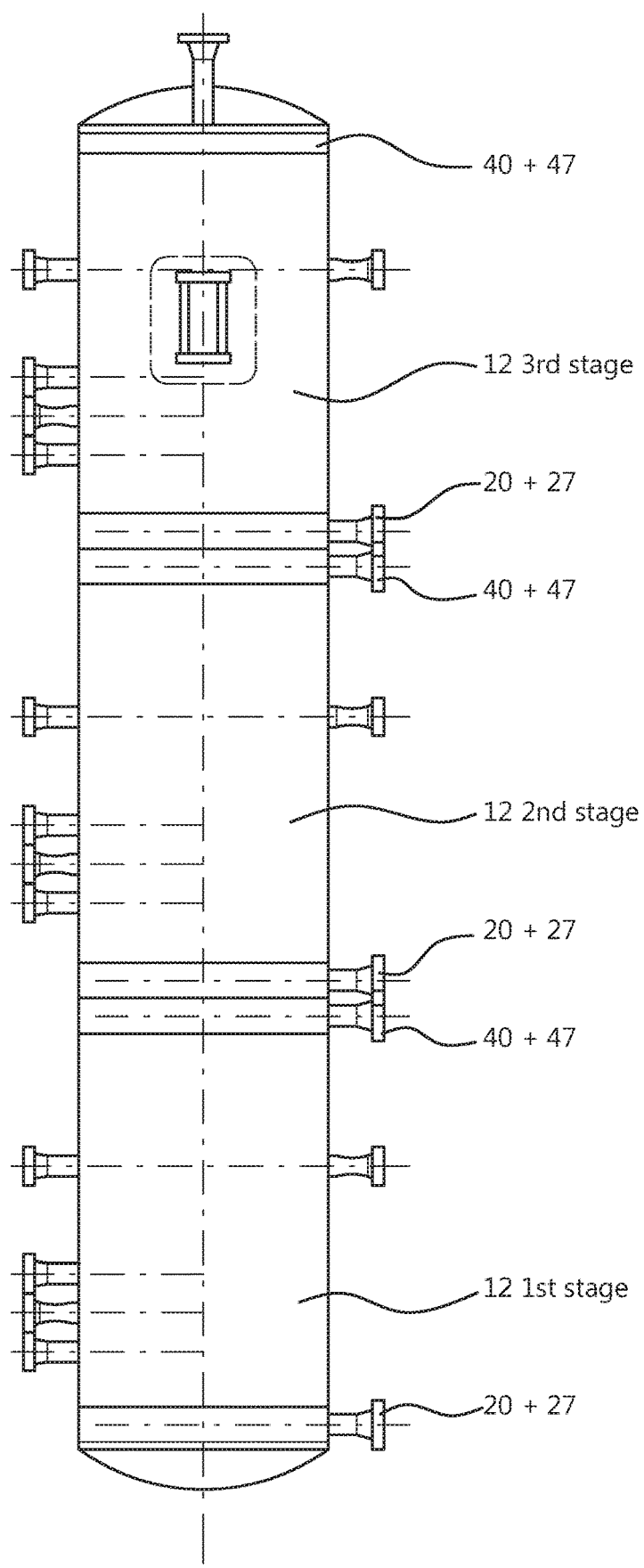
FIG. 5: Snapshot of upflow reactor drawing.
Figure 6:
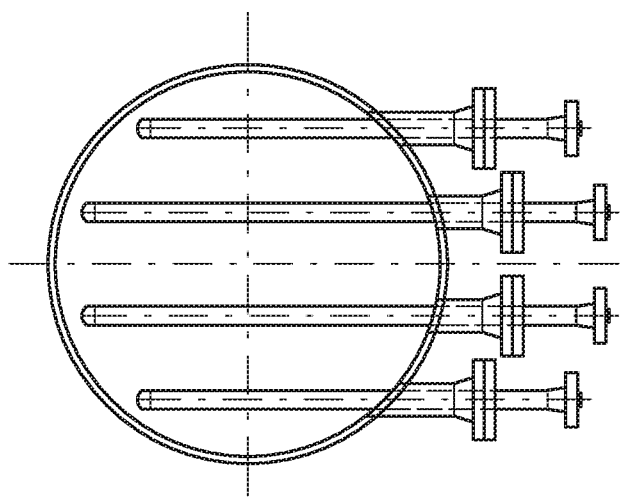
FIG. 6: Snapshot of side feed pipes below the distributor screen.
Figure 7:
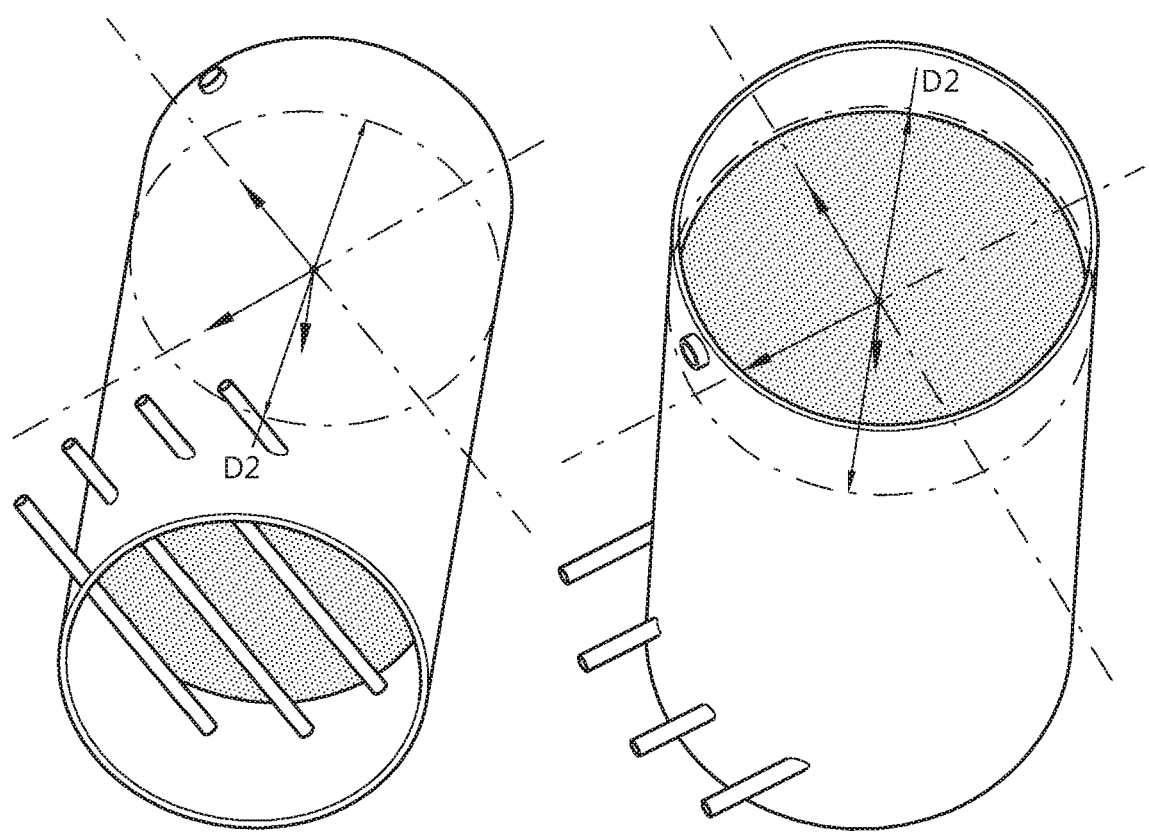
FIG. 7: Isometric view snap shots of 3D modelled geometry with bottom distributor screen (left) and top distributor screen (right).

An upflow test kit reactor was designed to have three catalyst bed sections. The total height of the reactor is about 4.4 metres and the diameter is about 0.74 metres. There are two solid partitions dividing the whole reactor into three sections. The schematics of one such section is shown in FIG. 4 (showing distributor 20, distributor screen 27, catalyst bed 12, collector screen 47, and collector 40) and the full schematic of the drawing is shown in FIG. 5 (showing a reactor with three reaction sections: a first stage reaction zone, a second stage reaction zone, and a third stage reaction zone, each having a catalyst bed 12). a distributor system with distributor 20 and distributor screen 27, a first stage reaction zone with catalyst bed 12, a collector system with collector 40 and collector screen 47, a second stage reaction zone with catalyst bed 12, and a third stage collector zone with catalyst bed 12). Each section of the reactor is provided with a distributor system comprising a distributor 20 and a distributor screen 27 and a collector system comprising a collector 40 and a collector screen 47. The distributor system is provided at the bottom of the section and the collector system is provided in the top of the section. Below distributor screen 27, a distributor 20 is provided in the form of a series of side feed pipes to distribute the liquid feed. These side feed pipes are arranged as shown in FIG. 6. Alternatively to the embodiment shown in FIG. 6, each of the side feed pipes may be distribution arms 32 that are attached to a single manifold 28 which enters the reactor, rather than separately entering the reactor (as in the embodiment of FIG. 2B). Each side feed pipe is provided with a set of perforations to distribute the feed across the cross-section. The isometric views of the modelled geometry is shown in FIG. 7.

Process Conditions

The raw materials for bisphenol A manufacture are phenol and acetone. The premixed feed of phenol and acetone are sent to the reactor as per the conditions given in table 1.

TABLE 1

Process conditions at the inlet and outlet

| | | Value | |
|---|---|---|---|
| Condition | Units | Inlet | Outlet |
| Mass flow | kg/h | 700 | 700 |
| Temperature | ° C. | 55-65 | 80-85 |
| Density | kg/m$^3$ | 1025 | 1033 |
| Viscosity | Pa · s | 4.4 | 4.4 |
| Surface Tension | N/m | 0.03 | 0.03 |

The most important information needed in the current problem is the flow distribution. The deviation from the uniform flow distribution which is referred to as mal-distribution is defined as expressed below.

$$maldistribution = \frac{\max Velocity - \min Velocity}{Average\ Velocity\ at\ a\ defined\ cross\ section}$$

At a distance of 10 mm above the bottom distributor plate, the mal-distribution is calculated and used as metric to compare across various design alternatives. The mal-distribution numbers at these cross sections are compared across different designs/scenarios to understand the flow behaviour (or reactor behaviour).

Example 1: Base Case Reactor with Two Distributors (Comparative)

A base case design, comprises four side feed pipes and two distributors. The four feed pipes were modelled with 46 perforations with a perforation diameter of 10 mm. The longer pipe was modelled with 13 perforations at 5 cm spacing and the shorter one was with 10 perforations with same spacing. Initially, perforations were made on the upper side of the tube (facing upwards). The distributor plate was modelled with 3825 number of smaller perforations with 5 mm diameter. The distributor screen is 7 mm thick.

Figure 8:
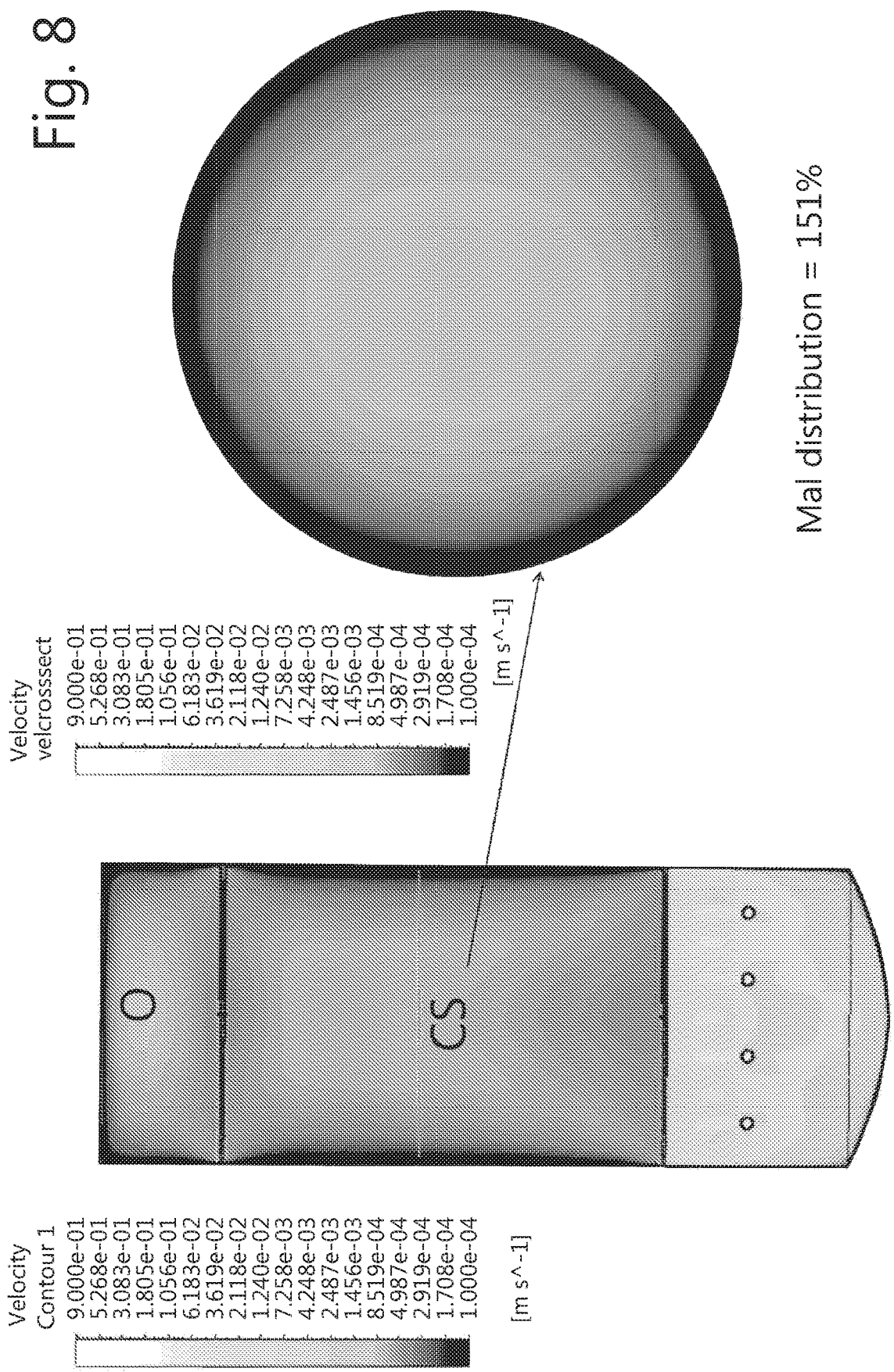
FIG. 8: Snapshot of velocity contours at a sectional centre plane (left) and the velocity contours at a mid-cross sectional plane (right) for base case design.
Figure 9:
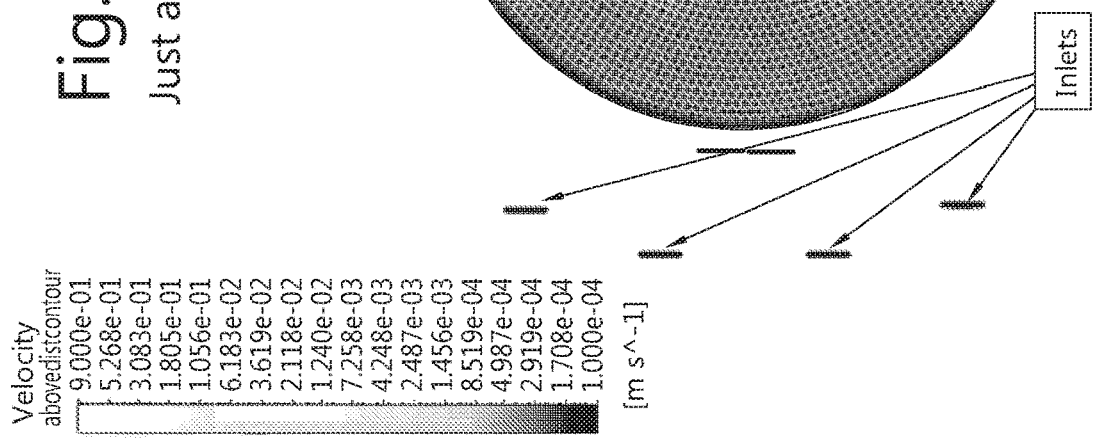
FIG. 9: Snap shot of velocity contours on a cross sectional plane located 10 mm above the distributor screen.

The cold flow simulations were done to the geometry with a design as explained in the previous paragraph and the results are shown in FIGS. 8 and 9. FIG. 8 shows the velocity contours of the base case design on a mid-axial sectional plane (left) and also at a mid-cross sectional plane (right). The velocity contours on the axial sectional plane indicated a developing flow and the velocity contours at the cross-sectional plane indicated a parabolic type of flow pattern. These results are as expected in a typical flow through pipe situation. The mal-distribution at the mid cross sectional plane was found to be 151% and it is due to the developing flow pattern with parabolic flow profile. The plane of interest for uniform flow distribution is just above the lower distributor screen. The velocity contours at a plane which is 10 mm above the lower distributor screen are as shown in FIG. 9. The mal-distribution is 189% and this high non-uniformity was attributed to the high velocity patches as highlighted in FIG. 9. The high velocity patches are believed to be due to the fact that more amount of fluid was trying to travel through the first perforation it encounters. These high velocity patches may lead to channeling in the catalyst bed as well.

Example 2: Change in Perforation Facing Direction to Dissipate Momentum

Figure 10:
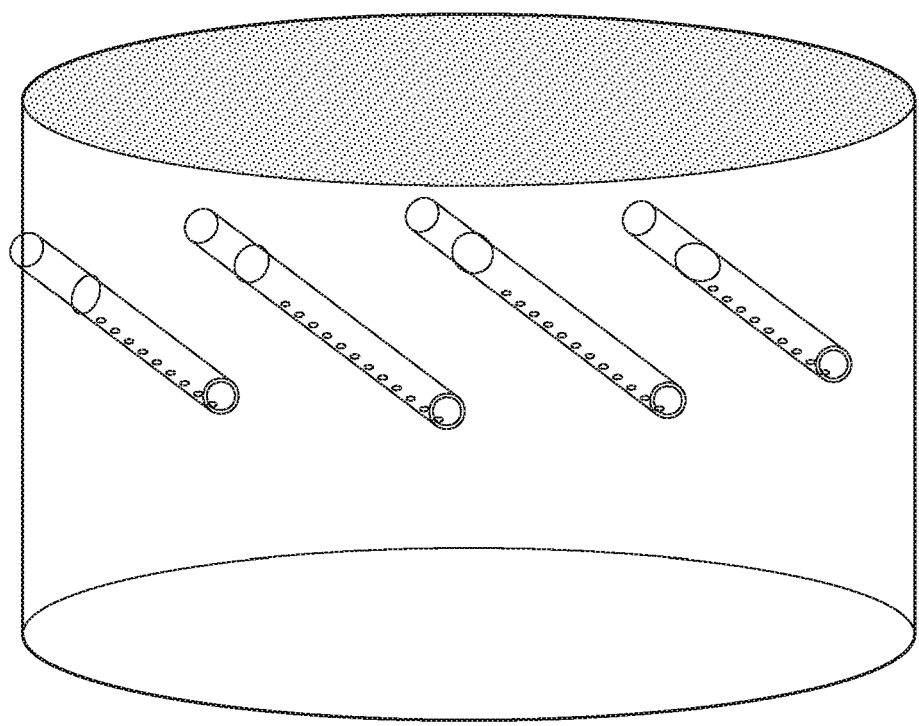
FIG. 10: Snapshot of modified geometry with perforations at the bottom face of feed pipes.

Based on the simulation results discussed for example 1, it was concluded that the high velocity patches are due to the fact that more fluid is trying to pass through the first perforation as it is the lower resistant path. This has resulted in high local velocities at the first aperture. It is possible to minimise the impact of high velocity patches on the catalyst bed by dissipating the momentum with an impingement plate. It was decided to dissipate the momentum using the bottom wall of the section as an impingement plate. This requires the placement of perforations at the bottom face of the side tubes such that fluid travels downward from these pipes and impinges on the bottom wall and dissipates the momentum. Modifications were done to the geometry model to pursue this and taken forward for the Computational Fluid Dynamics (CFD) simulations. A snap shot of modified geometry with perforations at the bottom face of the feed pipes is as shown in FIG. 10.

Figure 11:
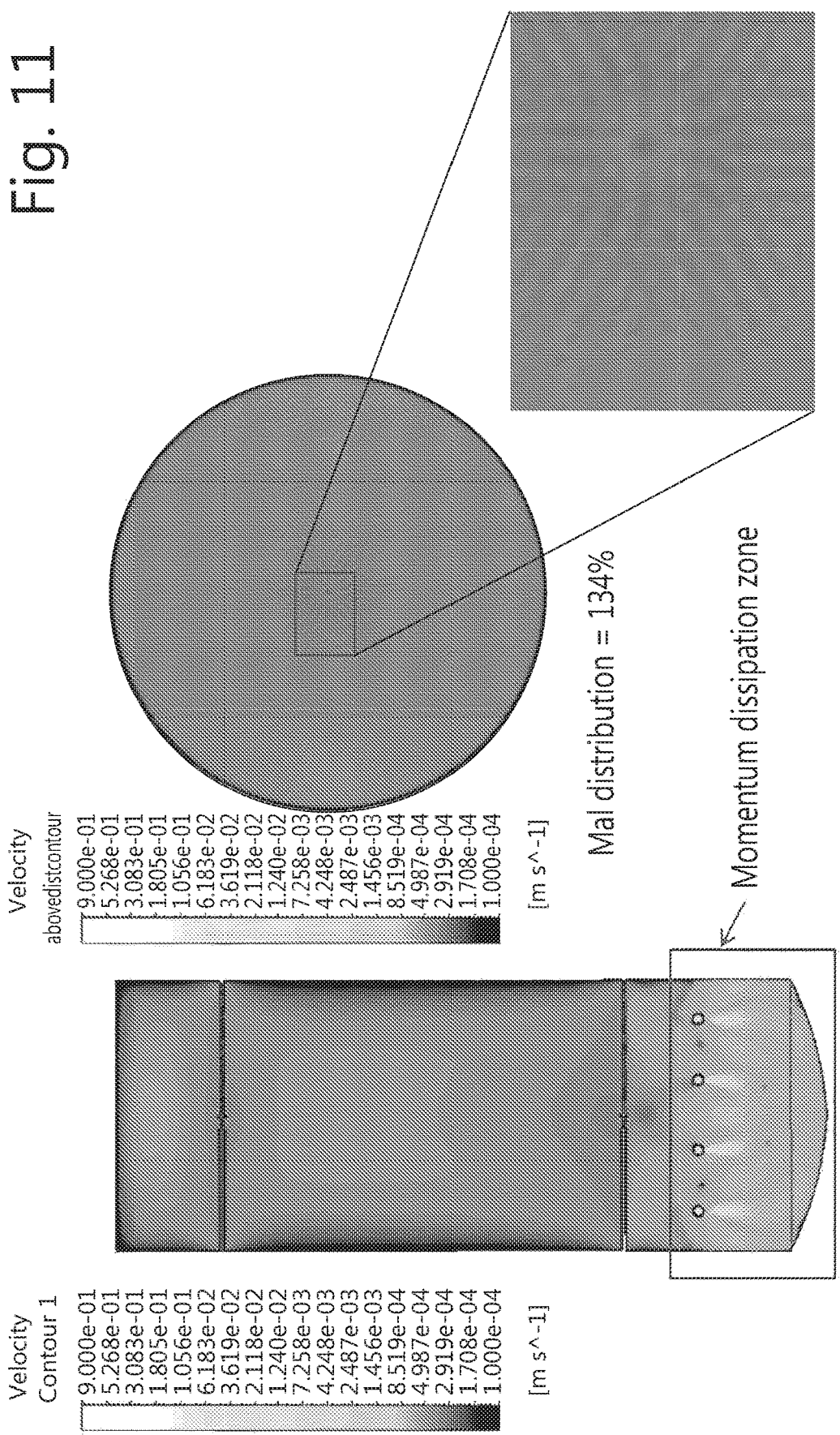
FIG. 11: Snapshot of velocity contours at a sectional centre plane (left) and the velocity contours at a cross sectional plane 10 mm above the bottom distributor screen (right).

CFD simulation results are shown in FIGS. 11 and 12. It was observed that when perforations are facing downwards, the fluid enters the reactor downward with higher velocities and the momentum of these smaller jets got dissipated in the zone below the feed pipes due to their impingement on the bottom wall of the section. The fluid after losing its momentum travels upward without disturbing the reaction section (where catalyst bed will be placed). Due to this, the mal-distribution has decreased significantly and the higher velocity patches were found to disappear in the velocity contours just above the lower distributor screen. This is evident as shown in FIGS. 11 and 12. The mal-distribution has come down significantly as shown in FIG. 12.

Example 3: Effect of Number of Distributor Screens

Figure 13:
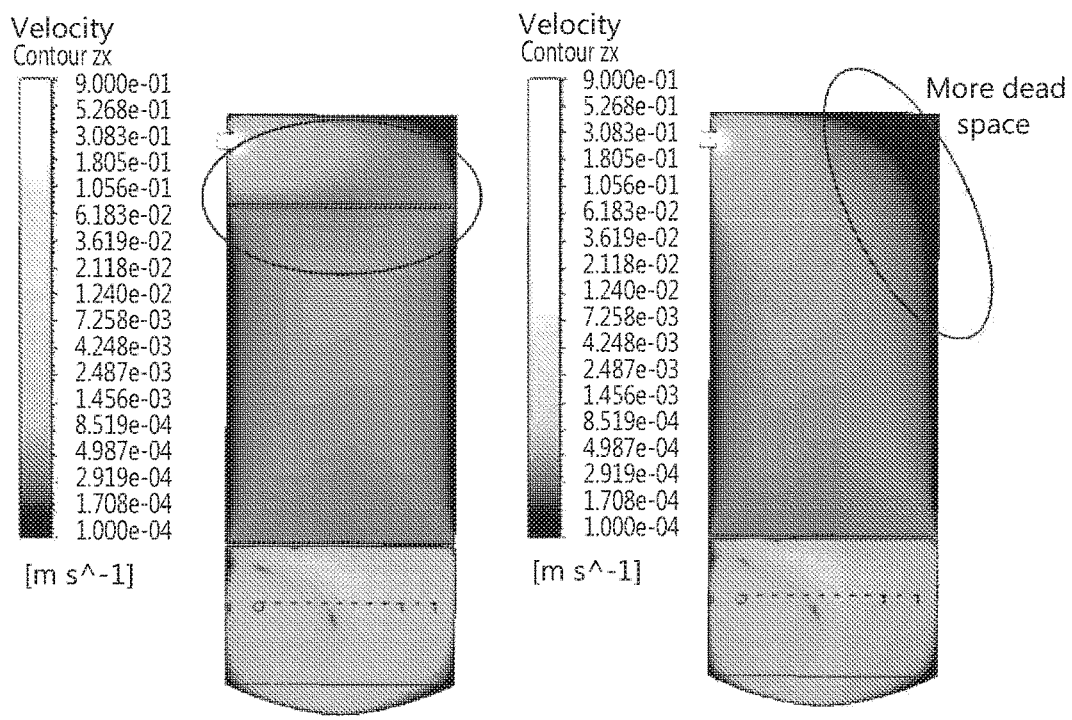
FIG. 13: Snapshot comparison of velocity contours on a centre sectional plan; with two distributor screens (left) and with one distributor screen (right).
Figure 14:
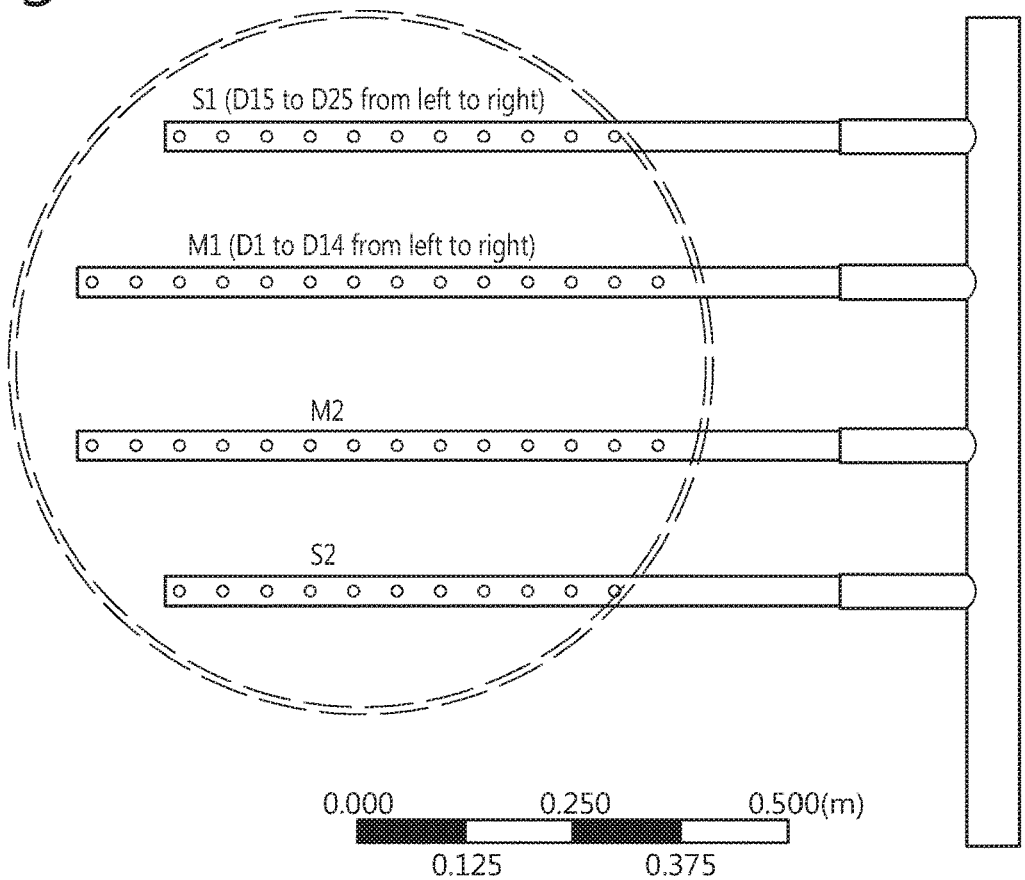
FIG. 14: Geometry model of pipe network model.

Geometry model was developed with one and two distributor screens and CFD simulations were done to understand the role of the additional distributor screen. The simulation results are shown in FIG. 13. It is clear that the distributor screen at the bottom is mainly to support the catalyst bed and also to help redistribute the fluid. But the role/need of the top distributor screen is in question without the support from CFD modelling. Based on the simulation results, it was found that the top distributor screen is playing a role in maintaining uniform flow even after the reaction section. As a result, the dead space in the reactor was minimised significantly. This is very critical for a good residence time distribution. In FIG. 13, the simulation results with a single distributor screen are compared with the results of two distributor screens and the smaller dead space is clearly evident when the top distributor screen was added.

Example 4: Pipe Network Model

In a feed distribution system, it is ideal to have uniform flow throughout the reactor cross section. In order to achieve good flow distribution across the cross section, it is needed to introduce the feed uniformly across the cross section. In order to distribute the feed effectively four feed pipes have been chosen with 50 perforations (46 in previous simulations). When the distribution system was modelled in this way, it was found that the amount of the feed that flows through these apertures varied significantly. It was understood that different lengths of flow paths were responsible for this behaviour. It is later thought that even though flow path lengths are different for different perforations, same flow can be achieved by playing with the perforation diameters. Here, CFD simulation work to achieve uniform flow through these perforations is discussed in detail.

To be computationally efficient, a pipe network model is modelled as the geometry so that the perforation diameters can be manipulated to assure the same liquid flow through every perforation. The visualised pipe network model geometry is shown in FIG. 15.

Simulations were done on the meshed geometry and the flow rates through every perforation of two pipes (M1 and S1) were monitored. The remaining two pipes (M2 and S2) were assumed to be identical as the first two (M1 and S1). The perforation diameters were changed by trial and error in order to maintain more or less uniform flow through these perforations. The velocity contours of the pipe network model as shown in FIG. 15. The velocity magnitude in the four pipes is very identical based on the colour legend. However, the numerical results are tabulated in Table 2. The total flow rate of 0.2 kg/s was equally distributed to all the feed pipes approximately. Since the number of perforations was different for longer pipe (M1) and shorter pipe (S1), the feed flow rate per perforation is different for these different pipes. The average feed flow rate for M1 pipe perforation is 0.00362 kg/s and for S1 pipe is 0.00438 kg/s. Another point to be noted is the variation along each pipe is minimised by trial and error simulation approach. For example, all the perforations in M1 pipe deliver pretty much the same flow rate and the same is true for S1 pipe as well. The standard deviation numbers were also computed and tabulated to highlight this conclusion. The remaining two pipes were assumed to be identical to reduce the computational intensity.

TABLE 2

Optimised perforation diameters and the flow rates

| Perforation | Diameter | M1 flow rate (kg/s) | Perforation | Diameter | S1 flow rate (kg/s) |
|---|---|---|---|---|---|
| D1 | 0.01 | 0.003798 | D15 | 0.009 | 0.004284 |
| D2 | 0.01 | 0.003721 | D16 | 0.009 | 0.004232 |
| D3 | 0.01 | 0.003617 | D17 | 0.009 | 0.004133 |
| D4 | 0.01 | 0.003521 | D18 | 0.095 | 0.004501 |
| D5 | 0.0105 | 0.003767 | D19 | 0.0095 | 0.004348 |
| D6 | 0.0105 | 0.003654 | D20 | 0.0095 | 0.004189 |
| D7 | 0.0105 | 0.003537 | D21 | 0.0098 | 0.004274 |
| D8 | 0.011 | 0.003742 | D22 | 0.0105 | 0.004674 |
| D9 | 0.011 | 0.003618 | D23 | 0.0105 | 0.004498 |
| D10 | 0.011 | 0.003595 | D24 | 0.011 | 0.004734 |
| D11 | 0.011 | 0.003565 | D25 | 0.0105 | 0.004338 |

TABLE 2-continued

Optimised perforation diameters and the flow rates

| Perforation | Diameter | M1 flow rate (kg/s) | Perforation | Diameter | S1 flow rate (kg/s) |
|---|---|---|---|---|---|
| D12 | 0.011 | 0.003529 | | | |
| D13 | 0.0108 | 0.003470 | | | |
| D14 | 0.0105 | 0.003519 | | | |
| | Mean | 0.003618 | | Mean | 0.004382 |
| | SD | 0.000104 | | SD | 0.000196 |

Set forth below are some examples of an upflow reactor as disclosed herein.

Embodiment 1: Use of an upflow reactor for producing a dihydroxy compound, said upflow reactor comprising: a vessel; a catalyst bed disposed in said vessel; a distributor in fluid communication with an inlet through which reactants are introduced to said distributor, said distributor being disposed at a lower end of said vessel and comprising a distributor perforation (preferably distributor perforations, e.g., a plurality of distributor perforations) disposed in said distributor, at least part of which distributor perforations are in a direction facing away from said catalyst bed; and a collector through which said product dihydroxy compound is removed, said collector being disposed at an upper end of said vessel.

Embodiment 2: The use according to Embodiment 1, wherein said reactor further comprises a distributor screen disposed between said distributor and said catalyst bed, wherein said distributor screen preferably comprises openings with a diameter of 50-300 μm and has a porosity of 10-50% open area.

Embodiment 3: The use according to any of the preceding embodiments, wherein said reactor comprises a second screen disposed at said collector, preferably wherein said second screen has a porosity of 10-50% open area.

Embodiment 4: The use according to embodiment 3, wherein said second screen comprises openings with a diameter of 50-300 μm.

Embodiment 5: The use according to any of the preceding embodiments, wherein said collector comprises one or more collector perforations disposed in said collector.

Embodiment 6: The use according to any of the preceding embodiments, wherein at least part of said collector perforations are in a direction facing away from the said catalyst bed.

Embodiment 7: The use according to any of the preceding embodiments, wherein the distributor perforation dimensions are such that the mass flow through each perforation is substantially the same.

Embodiment 8: The use according to any of the preceding embodiments, comprising 50 perforations per $m^2$ or more, such as 80 perforations per $m^2$ or more, preferably 100-200 perforations per $m^2$.

Embodiment 9: The use according to any of the preceding embodiments, further comprising at least one further distributor screen between said first distributor screen and said collector, wherein said further distributor screen preferably comprises openings with a diameter of 50-300 μm.

Embodiment 10: The use according to embodiment 9, wherein said further distributor screen has a porosity of 10-50% open area.

Embodiment 11: The use according to any of the preceding embodiments, wherein said vessel has a structural geometry that is substantially cylindrical, substantially parallelepiped, substantial spherical, or a combination thereof.

Embodiment 12: The use according to any of the preceding embodiments, wherein said distributor comprises a manifold in fluid communication with said inlet into which a reactant is received, and wherein a plurality of arms extend laterally from said manifold, wherein said one or more distributor perforations are disposed in said plurality of arms.

Embodiment 13: The use according to any of the preceding embodiments, wherein said collector comprises a manifold, wherein a plurality of arms extend laterally from said manifold, wherein said one or more collector perforations are disposed in said plurality of arms.

Embodiment 14: The use according to Embodiment 12 or 13, wherein said plurality of arms comprises arms disposed at opposing ends of said manifold and arms disposed intermediate said opposing ends of said manifold, wherein said arms disposed at said opposing ends of said manifold are shorter than said arms disposed intermediate said opposing ends of said manifold.

Embodiment 15: A method for producing a dihydroxy compound in an upflow reactor as defined in any one of Embodiments 1-13, said method comprising: introducing a reactant through said inlet to said distributor; flowing said reactant through said catalyst bed; and recovering said dihydroxy compound from said collector.

Embodiment 16: A method for manufacturing polycarbonate, said method comprising: producing a dihydroxy compound according to a method according to Embodiment 15, and reacting said dihydroxy compound with carbonate source, such as phosgene or diphenyl carbonate.

Embodiment 17: The use according to any one of Embodiments 1-14, or the method according to Embodiment 15 or 16, wherein said dihydroxy compound is a bisphenol, preferably bisphenol A.

The invention claimed is:

1. An upflow reactor, comprising:
   a vessel;
   a catalyst bed disposed in said vessel;
   a distributor in fluid communication with an inlet through which reactants for producing a dihydroxy compound are introduced to said distributor, said distributor being disposed at a lower end of said vessel and comprising a distributor perforation disposed in said distributor, at least part of which distributor perforation is in a direction facing away from said catalyst bed; and
   a collector through which the dihydroxy compound is removed, said collector being disposed at an upper end of said vessel.

2. The reactor according to claim 1, wherein said reactor further comprises a distributor screen disposed between said distributor and said catalyst bed.

3. The reactor according to claim 2, further comprising a further distributor screen between said distributor screen and said collector.

4. The reactor according to claim 2, wherein said distributor screen comprises openings with a diameter of 50 to 300 μm and has a porosity of 10 to 50% open area.

5. The reactor according to claim 1, wherein said reactor comprises a second screen disposed at said collector.

6. The reactor according to claim 5, wherein said second screen comprises openings with a diameter of 50 to 300 μm and has a porosity of 10 to 50% open area.

7. The reactor according to claim 1, wherein the distributor perforation dimensions are such that the mass flow through each perforation is substantially the same.

8. The reactor according to claim 1, wherein an amount of distributor perforations in the distributor is 50 perforations per $m^2$ or more.

9. The reactor according to claim 8, wherein the amount of distributor perforations is 80 perforations per $m^2$ or more.

10. The reactor according to claim 8, wherein the amount of distributor perforations is 100 to 200 perforations per $m^2$.

11. The reactor according to claim 1, wherein said collector comprises a collector perforation disposed in said collector.

12. The reactor according to claim 1, wherein said vessel has a structural geometry that is substantially cylindrical, substantially parallelepiped, substantial spherical, or a combination thereof.

13. The reactor according to claim 1, wherein said distributor comprises a manifold in fluid communication with said inlet into which a reactant is received, and wherein a plurality of arms extend laterally from said manifold, wherein said distributor perforation is disposed in said plurality of arms.

14. The reactor according to claim 1, wherein said collector comprises a manifold, wherein a plurality of arms extend laterally from said manifold, wherein said collector perforation is disposed in said plurality of arms.

15. The reactor according to claim 14, wherein said plurality of arms comprises arms disposed at opposing ends of said manifold and arms disposed intermediate said opposing ends of said manifold, wherein said arms disposed at said opposing ends of said manifold are shorter than said arms disposed intermediate said opposing ends of said manifold.

16. The reactor according to claim 1, wherein said dihydroxy compound is a bisphenol.

17. A method for producing a dihydroxy compound in an upflow reactor as defined in claim 1, said method comprising:
   introducing a reactant through said inlet to said distributor;
   flowing said reactant through said catalyst bed; and
   recovering said dihydroxy compound from said collector.

18. A method for manufacturing polycarbonate, said method comprising: producing a dihydroxy compound according to a method according to claim 17, and reacting said dihydroxy compound with carbonate source to form polycarbonate.

19. The method of claim 18, wherein the carbonate source is phosgene.

20. The method of claim 18, wherein the carbonate source is diphenyl carbonate.

* * * * *